United States Patent [19]

Maiti et al.

[11] Patent Number: 5,446,037
[45] Date of Patent: Aug. 29, 1995

[54] 2-[(SUBSTITUTED) METHYLENE] CEPHALOSPORIN SULFONES AS ANTIINFLAMMATORY, ANTIDEGENERATIVE AND ANTITHROMBIN AGENTS

[75] Inventors: Samarendra Maiti; Charles Fiakpui; A. V. N. Reddy; David Czajkowski; Paul Spevak; Harninder Atwal, all of Edmonton; Ronald G. Micetich, Sherwood Park, all of Canada

[73] Assignee: Synphar Laboratories, Inc., Alberta, Canada

[21] Appl. No.: 165,576

[22] Filed: Dec. 13, 1993

Related U.S. Application Data

[63] Continuation of Ser. No. 800,914, Dec. 5, 1991, abandoned.

[51] Int. Cl.⁶ .................. C07D 501/20; A61K 31/545
[52] U.S. Cl. ..................................... 514/201; 514/202; 514/204; 514/205; 540/221; 540/222; 540/225; 540/226
[58] Field of Search .............. 540/222, 221, 225, 226; 514/201, 202, 206, 204, 205

[56] References Cited

U.S. PATENT DOCUMENTS

| | | | |
|---|---|---|---|
| 4,547,371 | 10/1985 | Doherty et al. | 540/230 |
| 5,077,286 | 12/1991 | Bissolino et al. | 514/201 |
| 5,348,952 | 9/1994 | Bissolino et al. | 514/202 |
| 5,356,888 | 10/1994 | Alpegiani et al. | 514/204 |

OTHER PUBLICATIONS

Alpagiani et al., Bioorganic & Medicinal Chemistry Letters, vol. 2, No. 9, pp. 1127–1132, 1992.

*Primary Examiner*—Nicholas Rizzo
*Attorney, Agent, or Firm*—Nikaido, Marmelstein, Murray & Oram

[57] ABSTRACT

This invention relates to 2-[(substituted)methylene]-cephalosporin sulfones and in particular 2-[(heteroaryl substituted)methylene]cephalosporin sulfones which are effective elastase inhibitors as well as effective thrombin inhibitors and therefore are useful as anti-inflammatory, anti-degenerative and anti-thrombin agents.

30 Claims, No Drawings

2-[(SUBSTITUTED) METHYLENE] CEPHALOSPORIN SULFONES AS ANTIINFLAMMATORY, ANTIDEGENERATIVE AND ANTITHROMBIN AGENTS

This application is a continuation of application Ser. No. 07/800,914 filed Dec. 5, 1991, now abandoned.

FIELD OF THE INVENTION

This invention relates to 2-[(substituted)methylene]-cephalosporin sulfones and in particular 2-[(heteroaryl substituted)methylene]cephalosporin sulfones which are effective elastase inhibitors as well as effective thrombin inhibitors and therefore are useful as anti-inflammatory, anti-degenerative and anti-thrombin agents.

BACKGROUND OF THE INVENTION

Proteases are an important family of enzymes released from granulocytes, leukocytes and macrophages which are functional in a many standard biological activities, including digestion, formation and dissolution of blood clots, the formation of active forms of hormones, the immune reaction to foreign cells and organisms in pathological conditions. It has been reported that proteases from granulocytes and macrophages are responsible for chronic tissue destruction associated with inflammation, including rheumatoid arthritis and emphysema.

Azurophilic granules of human polymorphonuclear leukocytes (PMN) and macrophages release human leukocyte elastase (HLE), a serine protease which has a serine at its active site (Travis, J.; Salvesen, G. S. *Annu. Rev. Biochem.* 1983, 52,655). HLE has been reported to be capable of degrading the connective tissue component elastin as well as other connective tissue substrates and is implicated in the pathogenesis of a variety of inflammatory diseases, including pulmonary emphysema, rheumatoid arthritis, spondylitis, psoriasis, osteoarthritis, chronic bronchitis, cystic fibrosis, and respiratory distress syndrome. (Mittman, C., Ed., Pulmonary Emphysema and Proteolysis, Academic Press: New York, 1972; Janoff, A. Am. Rev. Respir. Dis. 1985, 132, 417; Morrison, H. M. Clin. Sci. 1987, 72, 151; Sprung et al., N. Engl. J. Med. 1981, 304 1301; Cochrane et al., J. Clin. Invest. 1983, 71, 754; Snider, G. L. Drug Dev. Res. 1987, 10,235; Jackson, et al., Eur. J. Respir. Dis. 1984, 65, 114; Suter et al., J. Infect. Dis. 1984, 149, 523; Velvart, M. Rheumatol. Int. 1981, 1, 121; and Ekerot et al., Adv. Exp. Med. Biol. 1984, 167, 335).

Under normal conditions, the proteolytic activity of proteases, including HLE, in the extracellular environment is inhibited by an excess of natural inhibitors, predominantly $\alpha_1$ protease inhibitor ($\alpha_1$ PI) and $\alpha_2$ macroglobulin. The natural inhibitors bind to the elastase and block the active site of the enzyme and because of their configurations, bind tightly to the enzyme. $\alpha_1$ PI is a glycoprotein found in human serum and exhibits inhibitory activity against elastase from the pancreas and from polymorphonuclear leukocytes. The inhibitor is hydrolyzed by the proteases to form a stable acyl enzyme in which the active site is no longer available.

However, pathological conditions can arise which disrupt the elastase-anti-elastase balance, resulting in an uncontrolled proteolysis of structural tissue, primarily in the lung and joints (Travis et al., supra). Marked reduction in serum $\alpha_1$ PI, either genetic or due to oxidants, has been associated with pulmonary emphysema which is characterized by a progressive loss of lung elasticity and respiratory distress. The loss of lung elasticity is caused by the progressive, uncontrolled proteolysis of the structure of the lung tissue by proteases such as elastase from leukocytes. (Powers, J. C., TIBS, 211, 1976). In addition, elastase has also been reported to participate in the progressive deterioration of articular cartilage resulting in rheumatoid arthritis. (Menninger, H. et al., Biological Functions of Proteinases, H. Holzer and H. Tschesche, eds. Springer-Verlag, Berlin, Heidelberg, N.Y., 1979, pp.196-206).

Accordingly, therapeutic compounds which act as elastase inhibitors have been developed. Among the most effective elastase inhibitors are cephalosporin sulfone derivatives.

U.S. Pat. No. 4,547,371 discloses the use of substituted cephalosporin sulfones as elastase inhibitors which have the structure shown below.

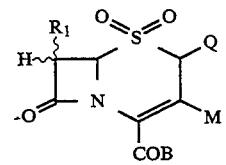

The C-2 position which is designated as Q is described as being hydrogen, $C_{1-6}$ alkyl, substituted or unsubstituted methylene, or unsubstituted or substituted phenylthio $C_{1-6}$ alkyl or phenylsulfonyl $C_{1-6}$ alkyl.

Hagmann et al., (1989) Eur. J. Med. Chem. 24:599–604 discloses the inhibition of human leukocyte elastase by C-2 substituted cephalosporin sulfones. The C-2 position in the structure shown below which is designated as $R_1$ is substituted with H, $CH_2$, $\alpha$-$CH_3$, $\beta$-$CH_3$, $CH_2SPh$, —$CH_2CH_2N_2$—, —$CH_2CH_2$— or $\alpha$-$OCH_3$.

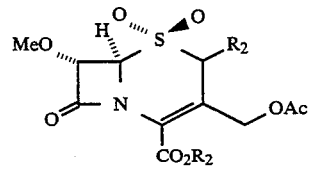

European Patent No. 0337704 discloses the use of 4-acylcephem sulfones as elastase inhibitors which have the structure shown below.

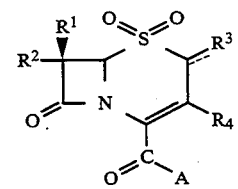

The C-2 position which is designated as $R_3$ is described as being a methylene group (=$CH_2$) or =$CHR^{IV}$, wherein $R_{IV}$ is either $C_1$-$C_4$ alkyl or phenyl, carboxy, $C_1$-$C_4$ alkyloxycarbonyl.

The present inventors have discovered that 2-[(substituted)methylene]cephalosporin sulfones, particularly 2-[(heteroaryl substituted)methylene]cephalosporin sulfones are highly useful as elastase inhibitors and thus can be used in the treatment of inflammatory and degenerative diseases caused by proteolytic enzymes in mammals. The present inventors have also discovered that the compounds of the present invention are highly useful as anti-thrombin agents in the prevention, control and treatment of blood clotting.

SUMMARY OF THE INVENTION sulfones and in particular 2-[(heteroaryl substituted)methylene]cephalosporin sulfones which are effective elastase inhibitors as well as effective thrombin inhibitors and therefore are useful as anti-inflammatory, anti-degenerative and anti-thrombin agents.

The structural formula of the cephalosporin sulfones of the present invention is represented as follows:

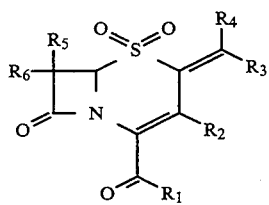

DETAILED DESCRIPTION OF THE INVENTION

The present inventors have discovered that 2-[(substituted)methylene]cephalosporin sulfones and in particular 2-[heteroaryl(substituted)methylene]cephalosporin sulfones are potent elastase inhibitors useful in the prevention, control and treatment of inflammatory and degenerative conditions as well as potent anti-thrombin agents useful in the control, prevention and treatment of blood clotting.

The structural formula of the cephalosporin sulfones of the present invention are represented as follows:

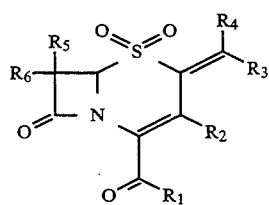

$R_1$ in the above-described formula may, for example, be $OR_a$. $R_a$ is preferably an optionally substituted $C_{1-6}$ alkyl group, an optionally substituted $C_{2-6}$ alkenyl group, an optionally substituted $C_{2-6}$ alkynyl, an optionally substituted $C_{3-6}$ cycloalkyl, a halogenated $C_{1-6}$ alkyl group, a $C_{1-6}$ alkoxy $C_{1-6}$ alkyl group, a $C_{1-6}$ alkanoyl $C_{1-6}$ alkyl group, a $C_{1-6}$ alkanoyloxy $C_{1-6}$ alkyl group, a $C_{6-10}$ aryl group, an aralkyl group, a heteroaryl group, a heteroarylalkyl group, a heterocyclyl group, a heterocyclylalkyl group or a like compound. The heterocyclic compounds are preferably saturated or unsaturated monocyclic or fused polycyclic 3–8 membered heterocyclic groups containing at least one hetero atom selected from O, S or N. In addition, groups represented by $R_a$ are preferably substituted with chloro, bromo, fluoro, hydroxy, alkoxy, amino, mercapto, nitro, cyano, carboxy, carboxamide, N-substituted carboxamide, sulfinyl, sulfonyl or alkoxycarbonyl or like compounds.

$R_1$ in the above-described formula may also be $NR_bR_c$. $R_b$ is preferably the same as $R_a$. Therefore, $R_b$ may, for example, be an optionally substituted $C_{1-6}$ alkyl group, an optionally substituted $C_{2-6}$ alkenyl group, an optionally substituted $C_{2-6}$ alkynyl, an optionally substituted $C_{3-6}$ cycloalkyl, a halogenated $C_{1-6}$ alkyl group, a $C_{1-6}$ alkoxy $C_{1-6}$ alkyl group, a $C_{1-6}$ alkanoyl $C_{1-6}$ alkyl group, $C_{6-10}$ alkyl group, a $C_{1-6}$ alkanoyloxy $C_{1-6}$ aryl group, an aralkyl group, a heteroaryl group, a heteroarylalkyl group, a heterocyclyl group, a heterocyclylalkyl group or a like compound. In addition, groups represented by $R_b$ are preferably substituted with chloro, bromo, fluoro, hydroxy, alkoxy, amino, mercapto, nitro, cyano, carboxy, carboxamide, N-substituted carboxamide, sulfinyl, sulfonyl or alkoxycarbonyl or like compounds.

$R_c$ may be hydrogen or may be the same as $R_a$. Therefore, $R_c$ may, for example, be an optionally substituted $C_{1-6}$ alkyl group, an optionally substituted $C_{2-6}$ alkenyl group, an optionally substituted $C_{2-6}$ alkynyl, an optionally substituted $C_{3-6}$ cycloalkyl, a halogenated $C_{1-6}$ alkyl group, a $C_{1-6}$ alkoxy $C_{1-6}$ alkyl group, a $C_{1-6}$ alkanoyl $C_{1-6}$ alkyl group, a $C_{1-6}$ alkanoyloxy $C_{1-6}$ alkyl group, $C_{6-10}$ aryl group, an aralkyl group, a heteroaryl group, a heteroarylalkyl group, a heterocyclyl group, a heterocyclylalkyl group or a like compound. In addition, group represented by $R_c$ are preferably substituted with chloro, bromo, fluoro, hydroxy, alkoxy, amino, mercapto, nitro, cyano, carboxy, carboxamide, N-substituted carboxamide, sulfinyl, sulfonyl or alkoxycarbonyl or like compounds.

In the formula of the present invention $NR_bR_c$, $R_b$ and $R_c$ taken together with the nitrogen atom may form part of a heteroaromatic ring or a heterocyclic ring. The heteroaromatic ring preferably contains from 2 to 7 carbon atoms and contains at least one hetero atom selected from the group consisting of N, S and O and may be substituted at the carbon or at the nitrogen atom. Representative examples of such heteroaromatic rings are:

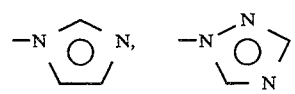

The heterocyclic ring preferably contains from 2 to 7 carbon atoms and contains at least one hetero atom selected from the group consisting of N, S and O and may be substituted at the carbon or at the nitrogen atom. Representative examples of such heterocyclic rings are:

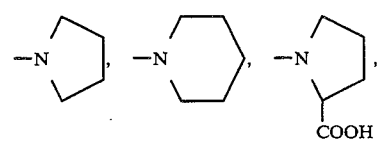

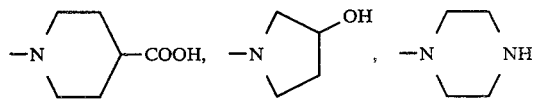

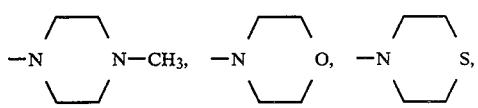

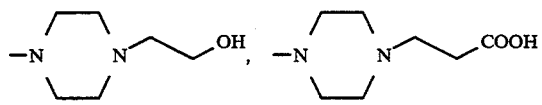

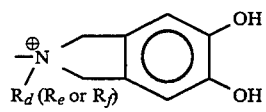

The aromatic heterocyclic ring preferably contains from 6 to 8 carbon atoms and contains at least one hetero atom selected from the group consisting of N, S and O. Representative examples of the aromatic heterocyclic ring are:

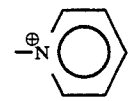

$NR_bR_c$ may also preferably be an amino acid, dipeptide or tripeptide moiety or like compound.

As representative examples, $R_1$ may be methoxy, ethoxy, isopropoxy, t-butoxy, allyloxy, methoxyethyloxy, benzyloxy, p-nitrobenzyloxy, p-methoxybenzyloxy, diphenylmethyloxy, 2,2,2-trichloroethyloxy, 1-pyrrolidinyl, piperidino, 2-carboxy-pyrrolidin-1-yl, 4-carboxy-piperidin-1-yl, piperazinyl, N-methyl piperazinyl, N-(2-hydroxyethyl)piperazinyl, N-(2-carboxyethyl)piperazinyl, morpholino, thiomorpholino, 1,3,4-triazol-1-yl, 1-imidazolyl or like compounds.

$R_2$ in the above-described formula may, for example, be hydrogen, chloro, bromo or flouro or a similar compound.

$R_2$ in the above-described formula may also be a $C_{1-6}$ alkyl group, an optionally substituted $C_{2-6}$ alkenyl group, an optionally substituted $C_{2-6}$ alkynyl group and a $C_{3-8}$ cycloalkyl group. The groups can be unsubstituted or substituted with appropriate groups. For example, the groups may be substituted with chloro, bromo or fluoro or similar compounds.

$R_2$ in the above-described formula may also be $-OR_d$ or $-S(O)_nR_d$. Preferably, n is 0, 1 or 2 and $R_d$ is hydrogen or a $C_{1-6}$ alkyl group, a $C_{3-8}$ cycloalkyl group, a $C_{6-10}$ aryl group, an aralkyl group, a heteroaryl group, a heteroarylalkyl group or a like compound.

$R_2$ in the above-described formula may also be $-CHO$, $-COOH$, $-C(O)R_d$, $-CH_2-O-R_d$, $-CH_2-S(O)_n-R_d$, $-CH_2-OC(O)R_d$, $-CH_2-SC(O)R_d$, $-CH_2OC(O)NH_2$, $-CH_2NR_dR_e$, $-CH_2N\oplus R_dR_eR_f$, $-CH_2-NH-C(O)R_d$ or a like compound. Preferably, $R_d$ is as previously defined above and $R_e$ and $R_f$ are the same as $R_d$. Therefore, $R_e$ and $R_f$ may, for example, be hydrogen or a $C_{1-6}$ alkyl group, a $C_{3-8}$ cycloalkyl group, a $C_{6-10}$ aryl group, an aralkyl group, a heteroaryl group, a heteroarylalkyl group or a like compound. Preferably, n is 0, 1 or 2.

$NR_dR_e$, $NR_eR_f$, $N\oplus R_dR_f$ or $NR_dR_eR_f$ is preferably a heterocyclic ring or an aromatic heterocyclic ring. The heterocyclic ring preferably contains from 4 to 8 carbon atoms and contains at least one hetero atom selected from the group consisting of N, S and O. Representative examples of the heterocyclic ring are:

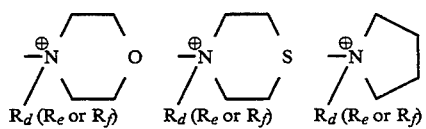

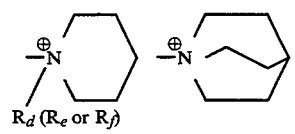

$R_2$ in the above-described formula may also be $-CH_2-S(O)_n-Het$ or a like compound. Preferably, n is 0, 1 or 2 and Het is one of the following compounds or a similar compound:

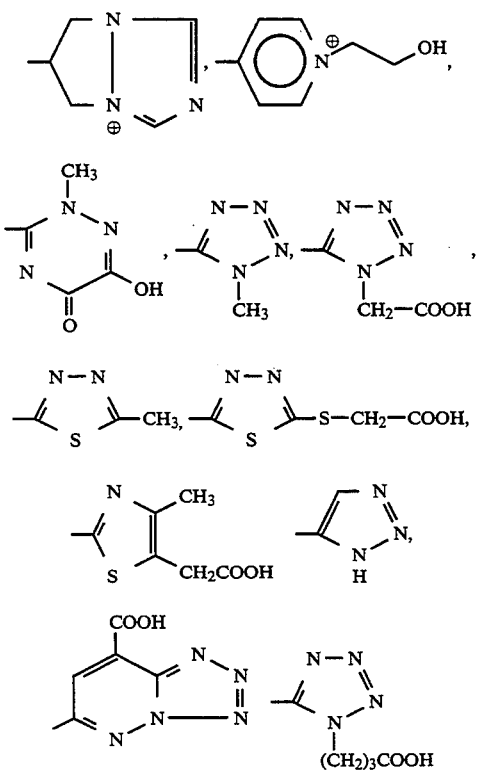

$R_2$ in the above-described formula may also be a heterocyclic ring selected from the following compounds or a like compound:

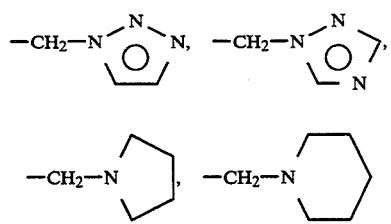

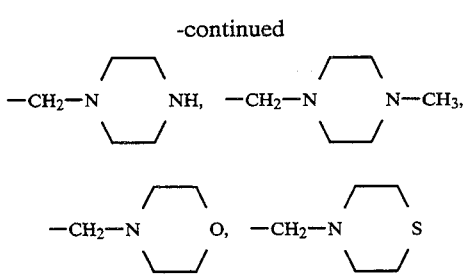

Preferably, $R_2$ may be hydrogen, methyl, trifluoromethyl, hydroxy, methoxy, vinyl, cyclopropyl, methylthio, acetoxymethyl, hydroxymethyl, chloromethyl, bromomethyl, carbamoyloxymethyl, methoxymethyl, phenoxymethyl, 3-pyridyloxymethyl, methylsufonylmethyl, phenylsulfonylmethyl, (1,2,3-triazol-1-yl)methyl, (1,2,4-triazol-1-yl)methyl, and aminomethyl or a like compound.

$R_2$ may also preferably be a quaternaryammonium methyl or like compound selected from the following compounds:

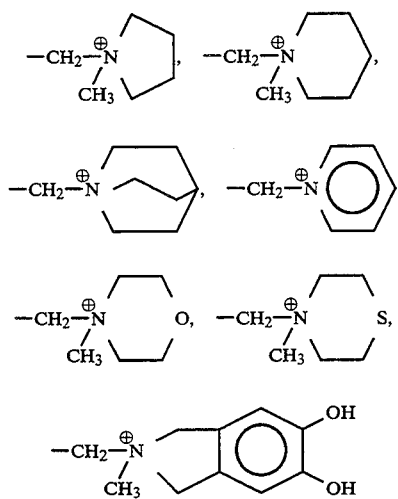

Representative examples of $R_3$ in the above-described formula are hydrogen; a $C_{1-6}$ alkyl group; a $C_{6-10}$ aryl group; a $C_{3-8}$ cycloalkyl group; an aralkyl group; a saturated or unsaturated monocyclic or fused polycyclic heterocyclic group; a halogenated $C_{1-6}$ alkyl group; a hydroxy $C_{1-6}$ alkyl group; —CH$_2$COOC$_{1-6}$ alkyl; —CH$_2$COOH or similar compounds. Preferably, the heterocyclic group has 3 to 8 carbon atoms and contains at least one hetero atom selected from the group consisting of O, S and N.

Preferably, $R_3$ in the above-described formula is a saturated or unsaturated monocyclic or fused polycyclic heterocyclic group. The heterocyclic group preferably contains from 3 to 8 carbon atoms and contains at least one hetero atom selected from the group consisting of O, S and N.

More preferably, $R_3$ in the above-described formula is a saturated or unsaturated monocyclic or fused polycyclic 3 to 8 membered heterocyclic group containing at least one hetero atom selected from the group consisting of O, S and N, and $R_4$ in the above-described formula is hydrogen; a $C_{1-6}$ alkyl group; a $C_{6-10}$ aryl group; a $C_{3-8}$ cycloalkyl group; an aralkyl group; a halogenated $C_{1-6}$ alkyl group; a hydroxy $C_{1-6}$ alkyl group; —CH$_2$COOC$_{1-6}$ alkyl; or —CH$_2$COOH or like compounds.

Representative examples of $R_3$ are methyl, isopropyl, t-butyl, cyclopropyl, phenyl, pyridyl, thienyl, furyl, N-methyl pyrrolyl, pyrazinyl, pyrimidinyl, quinolyl, isoquinolyl, oxazolyl, isoxazolyl, thiazolyl, isothiazolyl, 1-methyl-1,2,3-triazol-4-yl, 1-(2-hydroxyethyl)-1,2,3-traizol-4-yl, 1-(2-pyridinoethyl)-1,2,3-triazol-4-yl, 1-(2-morpholinoethyl)-1,2,3-triazol-4-yl, 1-(2-piperidinoethyl)-1,2,3-triazol-4-yl, or 1-(2-piperazinyl ethyl)-1,2,3-triazol-4-yl or like compounds.

$R_4$ in the above-described formula may, for example, be hydrogen or a $C_{1-6}$ alkyl group; a $C_{6-10}$ aryl group; a $C_{3-8}$ cycloalkyl group; an aralkyl group; a saturated or unsaturated monocyclic or fused polycyclic heterocyclic group; a halogenated $C_{1-6}$ alkyl group; a hydroxy $C_{1-6}$ alkyl group; —CH$_2$COOC$_{1-6}$ alkyl; —CH$_2$COOH or similar compounds. Preferably, the heterocyclic group has 3 to 8 carbon atoms and contains at least one hetero atom selected from the group consisting of O, S and N.

Preferably, $R_4$ in the above-described formula is a saturated or unsaturated monocyclic or fused polycyclic heterocyclic group. The heterocyclic group preferably contains from 3 to 8 carbon atoms and contains at least one hetero atom selected from the group consisting of O, S and N.

More preferably, $R_4$ in the above-described formula is a saturated or unsaturated monocyclic or fused polycyclic 3 to 8 membered heterocyclic group containing at least one hetero atom selected from the group consisting of O, S and N, and $R_3$ in the above-described formula is hydrogen; a $C_{1-6}$ alkyl group; a $C_{6-10}$ aryl group; a $C_{3-8}$ cycloalkyl group; an aralkyl group; a halogenated $C_{1-6}$ alkyl group; a hydroxy $C_{1-6}$ alkyl group; —CH$_2$COOC$_{1-6}$ alkyl; or —CH$_2$COOH or like compounds.

Representative examples of $R_4$ are methyl, isopropyl, t-butyl, cycloproplyl, phenyl, pyridyl, thienyl, furyl, N-methyl pyrrolyl, pyrazinyl, pyrimidinyl, quinolyl, isoquinolyl, oxazolyl, isoxazolyl, thiazolyl, isothiazolyl, 1-methyl-1,2,3-triazol-4-yl, 1-(2-hydroxyethyl)-1,2,3-traizol-4-yl, 1-(2-pyridinoethyl)-1,2,3-triazol-4-yl, 1-(2-morpholinoethyl)-1,2,3-triazol-4-yl, 1-(2-piperidinoethyl)-1,2,3-triazol-4-yl, or 1-(2-piperazinyl ethyl)-1,2,3-triazol-4-yl or like compounds.

$R_5$ in the above-described formula may, for example, be hydrogen, chloro, fluoro, bromo or iodo or may be a $C_{1-6}$ alkyl group; a $C_{2-6}$ alkenyl group; —OH; —OR$_g$; —OC(O)R$_g$; —OSO$_2$R$_g$; —NHC(O)R$_g$; NH—Z; —S-(O)$_n$R$_g$ or a similar compound. Preferably, n is 0, 1 or 2 and R$_g$ is the same as R$_d$. Therefore, R$_g$ may, for example, be a $C_{1-6}$ alkyl group, a $C_{3-8}$ cycloalkyl group, a $C_{6-10}$ aryl group, an aralkyl group, a heteroaryl group, a heteroarylalkyl group or a like compound. Z is preferably hydrogen or a mono, di- or tri-peptide composed of D or L amino acids with a terminal amino group either free or acylated by —C(O)R$_g$ or —C(O)OR$_g$, wherein R$_g$ is as previously defined;

Representative examples of $R_5$ are methoxy, ethoxy, methyl, ethyl, vinyl, formamido, acetamido, trifluoroacetamido, acetyloxy, chloroacetyloxy, bromoacetyloxy, methylsulfonyloxy, phenylsulfonyloxy, tolylsulfonyloxy or like compounds.

$R_6$ in the above-described formula may, for example, be hydrogen, chloro, bromo, methoxy or methylthio or like compounds.

The compounds of the present invention which are represented by the above-described formula are intended to include all geometrical isomers, including cis- and transisomers. Particularly, the compounds of the present invention include both geometrical isomers (cis- and trans-) at the C-2 position as represented in the following formulas:

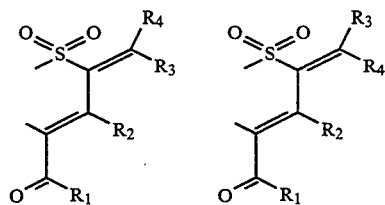

The present invention provides the salts of those compounds of formula (I) that have salt forming groups, especially the salts of the compounds having a carboxylic group, a basic group (e.g. an amino, piperazino, or guanidino group) or a quaternary ammonium group. The salts are especially physiologically tolerable salts, for example, alkali metal and alkaline earth metal salts (e.g. sodium, potassium, lithium, calcium and magnesium salts), ammonium salts and salts with an appropriate organic amine or amino acid (e.g. arginine, procaine salts) and the addition salts formed with suitable organic or inorganic acids, for example, hydrochloric acid, sulfuric acid, carboxylic and sulfonic organic acids (e.g. acetic, trifluoroacetic, p-toluene sulfonic acid). Some compounds of formula (I) which contain a carboxylate and an ammonium group may exist as zwitterions.

The present invention also includes those compounds of formula (I) that have suitably pharmaceutically acceptable in vivo hydrolysable esters namely those esters which hydrolyse in the human body to produce the parent acid or its salt. Examples of suitable in vivo hydrolysable ester groups include acetoxymethyl, pivaloyloxymethyl, α-acetoxymethyl, α-acetoxybenzyl, α-pivaloyloxyethyl, ethoxycarbonyloxymethyl, α-ethoxycarbonyloxyethyl and other groups well known in the penicillin and cephalosporin art.

The compounds of the present invention may exist in non-hydrated, hydrated or solvated form.

Preferred compounds of the present invention are t-butyl-3-acetoxymethyl-3-cephem-2-(1-methyl-1,2,3-triazol-4-yl)exomethylene-7α-methoxy-4-carboxylate-1,1-dioxide, t-butyl-3-acetoxymethyl-3-cephem-2-(2-fluorophenyl)exomethylene-7α-methoxy-4-carboxylate-1,1-dioxide, t-butyl-3-acetoxymethyl-3-cephem-2-(3-thienyl)exomethylene-7α-methoxy-4-carboxylate-1,1-dioxide, t-butyl-3-acetoxymethyl-3-cephem-2-(phenyl)exomethylene-7α-methoxy-4-carboxylate-1,1-dioxide, t-butyl-3-acetoxymethyl-3-cephem-2-(3-pyridyl)exomethylene-7α-methoxy-4-carboxylate-1,1-dioxide, t-butyl-3-methyl-3-cephem-2-(1-methyl-1,2,3-triazol-4-yl)exomethylene-7α-methoxy-4-carboxylate-1,1-dioxide, t-butyl-3-methyl-3-cephem-2-(methyl)exomethylene-7α-methoxy-4-carboxylate-1,1-dioxide, and t-butyl-3-acetoxymethyl-3-cephem-2-(2-furyl) exomethylene-7α-methoxy-4-carboxylate-1,1-dioxide.

The invention also relates to a process for preparing the compounds of the present invention. Preferably, the compounds of the present invention are prepared by the following route:

(a) reacting a cephem sulfone having structural formula II with carbonyl compound $R_3R_4CO$;

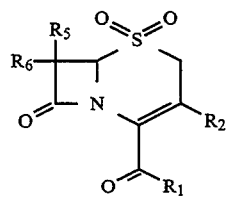

(b) obtaining from step (a) an intermediate having structural formula III;

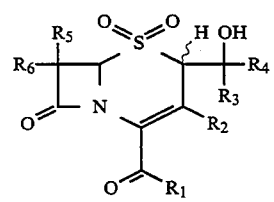

(c) converting the hydroxy group of said intermediate with structural formula III to leaving group $OR_7$;

(d) obtaining from step (c) an intermediate compound with structural formula IV;

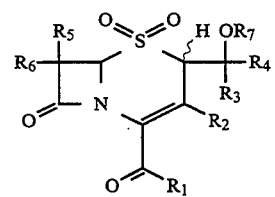

(e) subjecting said intermediate with structural formula IV to an elimination reaction; and (f) obtaining from step (e) two geometrically isomeric compounds having structural formula IA and IB

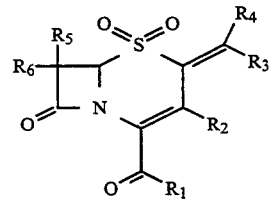

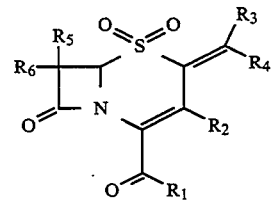

$R_1$–$R_6$ in the above scheme are as previously defined herein.

Preferably, to produce compounds of the present invention, cephem sulfone of the formula (II) is reacted with a carbonyl compound of the formula $R_3R_4CO$ to give a hydroxy intermediate of the formula (III). Preferably, the reaction is carried out in the presence of a base, preferably a non-nucleophilic base, and preferably a strong base. For example, suitable bases include lithium amide bases, lithium bistrimethylsilylamide, lithium dicyclohexylamide, lithium diisopropylamide, lithium 2,2,6,6-tetramethylpiperidide, lithium diphenylamide, and butyllithium. Preferably, solvents utilized in the reaction are aprotic organic solvents and more preferably, solvents are tetrahydrofuran, toluene, dimethoxyethane, dimethylformamide, and mixtures of two or more such solvents. The reaction is preferably carried out at a temperature range of from about −100° C. to ambient temperature, and more preferably, from −85° C. to 0° C., especially from −85° C. to −40° C. The reaction mixture may conveniently be quenched by adding a protic reagent, preferably an acid, such as acetic acid or citric acid, or water.

The hydroxy group of the intermediate (III) is converted to a leaving group having the formula $OR_7$. Preferably, $R_7$ is an appropriate reagent to form the desired substituted hydroxy derivative. Such reagents are preferably acetyl, methyl sulphonyl, trifluoromethyl sulfonyl, p-toluene sulphonyl, benzoyl, and the like. The conversions reaction may be carried out in the presence of a polar or non-polar, protic or aprotic, organic solvent. Preferably such solvents are dioxane, dimethoxyethane, methylene chloride, or tetrahydrofuran. The compounds of formula (IV) may exist in at least four isomeric forms at the C-2 and C-9 positions, and the stereochemistry may affect the ratio of isomers in the subsequent reaction.

The compound of the formula (IV), either as a separated isomer or as a mixture of isomers, is then subjected to an elimination reaction to eliminate the group $OR_7$ and to form two isomeric compounds IA and IB. Such elimination reactions are well known in the art. The elimination reaction may, for example, be carried out in the presence of a base (preferably, pyridine, triethyl amine) or in the presence of an acid (preferably, acetic acid or a mineral acid), suitably at a temperature range of from about −20° C. to about +40° C., and more preferably from about 0° C. to about 20° C. The reaction may be carried out in the presence of a polar or non-polar, protic or aprotic, organic solvent, preferably, dioxane, tetrahydrofuran, methylene chloride, and the like.

The final product is generally a mixture of isomers which may be isolated and purified in a conventional manner. Preferably, the product is isolated and purified by chromatographic techniques well known in the art.

The invention also relates to a method of treating inflammatory and degenerative diseases caused by proteolytic enzymes in mammals.

It has been found that the compounds of the present invention have an anti-inflammatory, anti-degeneration activity and are effective in the prevention and inhibition of edema and tissue formation as shown in Table 1 by the effective inhibition of the proteolytic function of human leukocyte elastase.

TABLE I

Activity of 2-[(substituted)methylene]cephalosporin sulfones against human leukocyte elastase (HLE).

| $R_1$ | $R_2$ | $R_3$ | $R_4$ | $R_5$ | $R_6$ | $IC_{50}(nM)$ |
|---|---|---|---|---|---|---|
| $Bu^t$ | OAc | H | CH$_3$-N-N=N-O (methyl-oxadiazole) | CH$_3$O | H | 7.8 |
| $Bu^t$ | OAc | CH$_3$-N-N=N-O (methyl-oxadiazole) | H | CH$_3$O | H | 9.2 |
| $Bu^t$ | OAc | H | 2-fluorophenoxy | CH$_3$O | H | 5.8 |
| $Bu^t$ | OAc | 2-fluorophenoxy | H | CH$_3$O | H | 6.0 |
| $Bu^t$ | OAc | H | pyridyloxy | CH$_3$O | H | 7.2 |

TABLE I-continued

Activity of 2-[(substituted)methylene]cephalosporin sulfones against human leukocyte elastase (HLE).

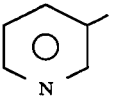

| $R_1$ | $R_2$ | $R_3$ | $R_4$ | $R_5$ | $R_6$ | $IC_{50}(nM)$ |
|---|---|---|---|---|---|---|
| $Bu^t$ | OAc | H | 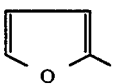 | $CH_3O$ | H | 7.2 |
| $Bu^t$ | OAc | 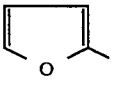 | H | $CH_3O$ | H | 22 |
| $Bu^t$ | OAc | H | 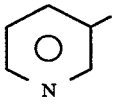 | $CH_3O$ | H | — |
| $Bu^t$ | $CH_3$ | 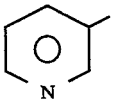 | H | $CH_3O$ | H | — |
| $Bu^t$ | $CH_3$ | H | 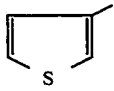 | $CH_3O$ | H | 35 |
| $Bu^t$ | OAc | 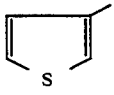 | H | $CH_3O$ | H | 6.4 |
| $Bu^t$ | OAc | H | 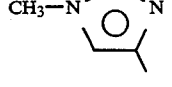 | $CH_3O$ | H | 6.4 |
| $Bu^t$ | $CH_3$ | 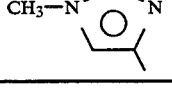 | H | $CH_3O$ | H | 100.0 |
| $Bu^t$ | $CH_3$ | H |  | $CH_3O$ | H | 75.0 |

Determining HLE Inhibitory Activity

Human leukocyte elastase (HLE) obtained from Elastin products, Missouri, U.S.A., is dissolved in 0.05M sodium acetate containing 0.4M sodium chloride (pH 5.3) and stored at −20° C. Small aliquots of these stock solutions (1 μm) are used in the HLE assays.

ASSAY CONDITIONS

Buffer: 0.01M Na, K-Phosphate, 0.5M NaCl (pH 7.6)
Substrate: 0,014M Meo-Suc-Ala-Ala-Pro-Val-pNA in DMSO
Temperature: 30° C.
Inhibitor: various concentrations in DMSO
Enzyme: stock solution noted above The stock solution of enzyme was equilibrated to 30° C. A cuvette containing buffer and inhibitor was equilibrated to 30° C. 10 μL of enzyme solution giving a rate of 0.04–0.05 AU/min in the absence of inhibitor, was mixed into the buffer/inhibitor solution and this mixture was incubated at 30° C. for 10 minutes. After this preincubation substrate was added to give a final concentration of 350 mM and a final DMSO concentration of 10% (v/v). The rate of product formation, proportional to the change in absorbance at 410 nm, was monitored for two minutes following the addition of substrate. For a typical IC$_{50}$ plot the rate was determined at 5–8 inhibitor concentrations (in duplicate) spanning 10–80% inhibition (in most cases). In most cases the data could be fit by linear least-squares and the IC$_{50}$ determined from this plot.

The text data in Table 1 clearly demonstrates that the compounds of the present invention exhibit anti-elastase activity and thus are effective elastase inhibitors.

The present invention further relates to a method of treating blood clotting in patients using compounds of the present invention.

It has been found that the compounds of the present invention have anti-thrombin activity and are effective in the prevention, control and treatment of blood clotting as shown in Table II by the effective inhibition of the thrombin.

TABLE II

| R$_1$ | R$_2$ | R$_3$ | R$_4$ | R$_5$ | R$_6$ | % inhibition at 10 μM |
|---|---|---|---|---|---|---|
| Bu$^t$ | OAc | 2-furyl | H | CH$_3$O | H | 94.7 |
| Bu$^t$ | OAc | 2-thienyl | H | CH$_3$O | H | 98.9 |
| Bu$^t$ | OAc | H | 2-fluorophenyl | CH$_3$O | H | 96.8 |
| Bu$^t$ | OAc | 2-fluorophenyl | H | CH$_3$O | H | 98.5 |

Determining the Inhibition of Thrombin

Lyophilized human plasma thrombin obtained from Boehringer, Montreal, Canada was dissolved in 0.5M Na, K-phosphate buffer (pH 7.0) and stored at +4° C.

ASSAY CONDITIONS

Buffer: 50 mM Tricine (pH 8.6), 500 mM NaCl, 0.1% PEG 8000
Substrate: 0.5 mM Chromozym TH (tosyl-glycyl-prolylarginine-4-nitroanilide acetate) in DMSO
Inhibitor: 10 μM dissolved in DMSO
DMSO: 10% (v/v)
Temperature: room temperature (approx.).

A single inhibitor concentration (10 μM) was tested using a spectrophotometric end-point assay (1 ml final volume). Enzyme activity was monitored by formation of a product that absorbed light at 410 nm and an enzyme concentration which gave a rate of 0.01–0.02 AU/min was used. Enzyme and inhibitor were pre-incubated for 10 min in the final amounts of buffer and DMSO. The reaction was then started by the addition of substrate. After 30 min incubation the reaction was terminated by the addition of 10% SDS (0.1 ml) and the absorbance measured. Enzyme blanks were run concurrently to account for any background absorbance by the compound. Inhibition was calculated by the net A$_{410}$ in the presence of inhibitor compared to that in the absence of inhibitor (DMSO controls).

The test data in Table II clearly demonstrates that the compounds of the present invention exhibit between 94.7 and 98.5% inhibition of thrombin at 10 μM and thus are effective thrombin inhibitors.

The compounds of the present invention can be used in the treatment of inflammatory and degenerative diseases caused by proteolytic enzymes in mammals, including humans. The compounds are Useful to prevent or arrest the progression of diseases such as emphysema, rheumatoid arthritis, osteoarthritis, cystic fibrosis, spondylitis, gout, psoriasis, chronic bronchitis, acute respiratory distress syndrome. The compounds of the present invention are also useful to prevent blood clotting.

The compounds of the present invention may be administered to a warm-blooded mammalian in need thereof, particularly a human, by oral, parental, topical, rectal administration or by inhalation. The compound may be conventionally formulated in an oral or parenteral dosage form compounding about 10 to about 250 mg per unit of dosage with a conventional vehicle, excipient, binder, preservative, stabilizer, flavor, color, sweetening agent or the like as called for by accepted pharmaceutical practice.

For parental administration, a 1 to 10 ml intravenous, intramuscular or subcutaneous injection would be given in an amount of about 0.02 to 10 mg/kg of body weight of a compound of the present invention three to four times daily. The injection would contain a compound of the present invention in an aqueous isotonic sterile solution or suspension optionally with a preservative such as phenol or a solubilizing agent such as ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as fixed oil in the preparation of injectables.

For rectal administration, the compounds of the present invention can be prepared in the form of suppositories by mixing with a suitable non-irritating excipient such as cocoa butter or polyethylene glycols.

For topical use, the compounds of the present invention can be prepared in the form of ointments, jellies, solutions or suspensions.

In a powdered aerosol, compounds of the invention may be administered by a spinhaler turbo-inhaler device obtained from Fisons Corporation of Bedford, Massachusetts, at a rate of about 0.1 to 50 mg per capsule, 1 to 8 capsules being administered daily for an average human. In a liquid aerosol, the compounds of the present invention are administered at the rate of about 100 to 1000 micrograms per "puff" or activated release of a standard volume of propellant. The liquid aerosol would be given at the rate of 1 to 8 "puffs" per day with variation in dosages due to the severity of the conditions being treated, the weight of the patient and the particle size distribution of the aerosol. A fluorinated hydrocarbon or isobutane find use as propellants for liquid aerosols.

Daily dose are in the range of about 0.01 to about 100 mg per kg of body weight, depending on the activity of the specific compound, the age, weight, sex and conditions of the subject to be treated, the type and severity of the disease, the frequency and route of administration. As would be well known, the amount of active ingredient that may be combined with the carried materials to produce a single dosage will vary depending upon the host treated and the particular mode of administration.

The following examples demonstrate the utility of the invention. The examples are not limiting, but are illustrative only, and modifications which would be apparent to those skilled in the art are included within the scope of this disclosure.

EXAMPLE-1 t-Butyl-3-acetoxymethyl-3-cephem-2-(1-methyl-1,2,3-triazol-4-yl)-exomethylene-7α-methoxy-4-carboxylate-1,1-dioxide To a solution of diphenylamine (0.993 g, 5.86 mmol) in dry THF (32 ml) cooled to −10° C. was added n-butyl lithium (1.6M in hexane, 3.7 ml, 5.89 mmol) and the solution was stirred under nitrogen at −10° C. for 5 min and at room temperature for 15 min. The reaction mixture was cooled to −78° C. at which time t-butyl-3-acetoxymethyl-3-cephem-7α-methoxy-4-carboxylate 1,1-dioxide (2.03 g, 5.41 mmol) in dry THF (16 ml) was added dropwise. The mixture was stirred for 15 min and then 1-methyl-1,2,3-triazol-4-carboxaldehyde (0. 654 g, 5.89 mmol) in dry THF (24 ml) was added dropwise. The mixture was stirred for 10 min. Acetic anhydride (1.52 ml, 16.1 mmol) in THF (8 ml) was added dropwise and stirred for 10 min at which time pyridine (0.48 ml, 5.93 mmol) was added. The reaction mixture was stirred at −78° C. for 15 min and at room temperature for 1 h; ice-water (25 ml) was added and the mixture was extracted with ethyl acetate (150 ml), the aqueous layer was re-extracted with ethyl acetate (50 ml). The combined ethyl acetate layers were washed with brine, dried (Na$_2$SO$_4$) and concentrated under reduced pressure to give 4.15 g of the crude product which was purified over a silica gel column using hexane-ethyl acetate mixture as eluant (3:2). Fast eluting components were unreacted cephem sulfone (480 mg) and triazole aldehyde (230 mg). Further elution of the column gave the cisisomer (360 mg) as the minor product followed by trans-isomer (1.08 mg) as the major product.

A portion of the cis-isomer (20 mg) was crystallized from ethyl acetate-hexane (12 mg), m.p. 180°–182° C., decomp. $^1$H NMR (200 MHz, CDCl$_3$) σ8.56 (s, 1H, triazole), 7.57 (s, 1H, olefin), 5.43 (d, 1H, J=13 Hz), 5.31 (d, 1H, J=1.5 Hz), 4.81 (d, 1H, J=13 Hz), 4.81 (d, 1H, J=1.5 Hz), 4.16 (s, 3H, N—CH$_3$), 3.59 (s, 3H, OCH$_3$), 2.09 (s, 3H, OCOCH$_3$), 1.58 (s, 9H, Bu$^t$).

Major isomer was obtained as a white foam. $^1$H NMR (200 MHz, CDCl$_3$) σ7.78 (s, 1H, triazole), 7.64 (s, 1H, olefin), 5.51 (d, 1H, J=13.5 Hz, CH$_2$OCOCH$_3$), 5.09 (d, 1H, J=2 Hz, H-7), 5.05 (d, 1H, J=13.5 Hz, CH$_2$O-COCH$_3$), 4.84 (d, 1H, J=2 Hz, H-6), 4.16 (s, 3H, N—CH$_3$), 3.57 (s, 3H OCH$_3$), 1.95 (s, 3H, OCOCH$_3$), 1.57 (s, 9H, Bu$^t$).

EXAMPLE-2 t-Butyl-3-acetoxymethyl-3-cephem-7α-methoxy-2(2-fluorophenyl)exomethylene-4-carboxylate1,1-dioxide A solution of diphenylamine (0.498 g, 2.94 mmol) in THF (16 ml) was cooled to −10° C. under nitrogen, n-butyllithium (1.6M in hexane, 1.84 ml, 2.94 mmol) was added dropwise and the reaction mixture was stirred at this temperature for 5 min and then at room temperature for 15 min. The mixture was cooled to −78° C. and cephem sulfone (1.0 g, 2.67 mmol) in THF (8 ml) was added dropwise. The resulting mixture was stirred for 15 min at which time 2-fluorobenzaldehyde (0.431 g, 3.47 mmol) in THF (12 ml) was added dropwise and the solution was stirred for 10 min; acetic anhydride (0.76 ml, 8 mmol) in THF (4 ml) was added dropwise and stirred for 10 min at which time pyridine (0.24 ml, 2.97mmol) was added. The resulting mixture was stirred for 15 min and then at room temperature for 1 h; ice water (25 ml) was added dropwise and the mixture was poured into ethyl acetate (100 ml). The ethyl acetate layer was separated and the aqueous layer was extracted with ethyl acetate (50 ml). The combined ethyl acetate layers were washed with brine, dried and concentrated. The residue was purified by column chromatography on a silica gel column using hexaneethyl acetate mixture (1:2) as eluant. Diphenylamine and unreacted 2-fluorobenzaldehyde were eluted first followed by the minor isomer (cis isomer, 0.247 g). The major isomer (trans isomer) was eluted next (0.656 g). The unconsumed starting cephem sulfone (0.27 g) was eluted last from the column.

$^1$H NMR (200 MHz CDCl$_3$ of the major (trans) isomer; σ7.89 (s, 1H, olefin), 7.14–7.53 (m, 4H, aromatic), 5.19 (d, 1H, J=2 Hz), 4.93 (d, 1H, J=2 Hz), 4.46 and 4.87 (AB$_q$, 2H, J=13 Hz), 3.59 (s, 3H, OCH$_3$), 1.91 (s, 3H, OCOCH$_3$), 1.56 (s, 9H, Bu$^t$).

$^1$H NMR (200 MHz, CDCl$_3$) of the minor (cis) isomer σ, 7.63–7.70 (m, 1H, aromatic), 7.53 (s, 1H, olefin), 7.36–7.49 (m, 1H, aromatic), 7.06–7.24 (m, 2H, aromatic), 5.25 (d, 1H, J=2 Hz), 4.81 (d, 1H, J=2 Hz), 4.73 and 5.48 (AB$_q$, 2H, J=13 Hz), 3.51 (s, 3H, OCH$_3$), 2.11 (s, 3H, OCOCH$_3$), 1.59 (s, 9H, Bu$^t$).

EXAMPLE-3 t-Butyl-3-acetoxymethyl-3-cephem-7α-methoxy-2-(3-thienyl)exomethylene-4-carboxylate 1,1-dioxide To a solution of diphenylamine (0.249 g, 0.00147 mol) in dry THF (8 ml) cooled to −10° C. under nitrogen was added n-butyl lithium (1.6M in hexane, 0.92 ml, 0.00147 mol) dropwise. The solution was stirred at −10° C. for 5 min and at room temperature for 15 min. The mixture was cooled to −78° C. and cephem sulfone (0.5 g, 0.00133 mol) in THF (4 ml) was added dropwise. The solution was stirred for 15 min at which time 3-thiophene carboxaldehyde (0.149 g, 0.00133 mol) in THF (6 ml) was added. The resulting mixture was stirred at −78° C. for 5 min and then at −22° C. for 10 min. Acetic anhydride (0.38 ml, 0.00399 mol) in THF (2 ml) was added and stirred for 10 min, pyridine (0.12 ml, 0.00133 mol) was added and the solution was stirred at −22° C. for 15 min and at room temperature for 1 h; ice water (20 ml) was added and was extracted with ethyl acetate. The combined ethyl acetate layers were washed with brine, dried (Na$_2$SO$_4$) and concentrated (1.13 g) which was purified over a silica gel column using dichloromethane-ethyl acetate as eluant. Fast moving component was diphenylamine followed by unreacted 3-thiophenecarboxaldehyde. Then the desired product was obtained as a mixture of geometrical isomers (100 mg, yellow amorphous solid, the ratio of E:Z was 3:1 as indicated from the $^1$H NMR).

$^1$H NMR (200 MHz, CDCl$_3$) of the major (trans) isomer $\sigma$; 7.74 (s, 1H, olefin), 7.56 (br, s, 1H, thiophene), 7.39–7.43 (m, 1H, thiophene), 7.11 (d, 1H, thiophene), 5.10 (d, 1H, J=1.84 Hz), 4.86 (d, 1H, J=1.84 Hz), 4.59 and 5.14 (AB$_q$, 2H, J=13.4 Hz), 3.57 (s, 3H, OCH$_3$), 1.95 (s, 3H, OCH$_3$), 1.57 (s, 9H, Bu$^t$).

$^1$H NMR (200 MHz, CDCl$_3$) of the minor (cis) isomer $\sigma$; 7.89 (br, s, 1H, thiophene), 7.45 (d, 1H, J=5.2 Hz, thiophene), 7.30–7.40 (m, 1H, thiophene), 7.33 (s, 1H, olefin), 5.29 (d, 1H, J=1.8 Hz), 4.75 (d, 1H, J=1.8 Hz), 4.85 and 5.45 (AB$_q$, 2H, J=13 Hz), 3.55 (s, 3H, OCH$_3$), 2.09 (s, 3H, OCOCH$_3$), 1.58 (s, 9H, Bu$^t$).

EXAMPLE-4 t-Butyl-3-acetoxymethyl-3-cephem-7α-methoxy-2-(phenyl)exomethylene-4-carboxylate 1,1-dioxide A solution of diphenylamine (0.249 g, 0.00147 mol) in dry THF (8 ml) was cooled to −10° C., 1.6 (M) solution of n-BuLi in hexane (0.92 ml, 0.00147 mol) was added. After stirring for 5 min at −10° C. the cooling bath was removed and stirred at room temperature for 15 min. The reaction mixture was then cooled to −78° C. and stirred for 10 min at which time a solution of t-butyl 3-acetoxymethyl-3-cephem-7α-methoxy-4-carboxylate 1,1-dioxide (0.5 g, 0.00133 mol) in THF (4 ml) was added dropwise. The reaction mixture was stirred at −78° C. for 15 min, then a solution of benzaldehyde (0.146 g, 0.00137 mol) in dry THF (6 ml) was added dropwise and stirred at −78° C. for 15 min and then allowed to raise up to −22° C. The color of the solution changed from light green to light brown. Acetic anhydride (0.38 ml) in dry THF (2 ml) was added and stirred for 10 minutes, then pyridine (0.12 ml, 0.00133 mol) was added and the mixture was stirred at −20° C. for 10 min and at room temperature for 1 h. The mixture was quenched with ice water (15 ml), extracted with ethyl acetate, washed with brine, dried and concentrated to give an oil (1.3 g) which was purified on a silica gel column using hexane-ethyl acetate mixture (3:1) as eluant. Early fractions (120 mg) was the desired product as a mixture of trans- and cis-isomers (from the $^1$H NMR spectrum the ratio of trans- and cis-isomers is approximately 4:1). The latter fractions were the recovered starting material (150 mg).

$^1$H NMR (200 Hz, CDCl$_3$) of the major (trans) isomer $\sigma$: 7.86 (s, 1H, olefin), 7.3–7.6 (m, 5H, aromatic), 5.16 (d, 1H, J=1.97 Hz, H-7), 4.91 (d, 1H, J=1.97 Hz, H-6), 4.43 and 4.95 (AB$_q$, 2H, J=13.3 Hz), 3.58 (s, 3H, OCH$_3$), 1.89 (s, 3H, OCOCH$_3$), 1.56 (s, 9H, Bu$^t$).

$^1$H NMR (200 MHz, CDCl$_3$) of the minor (cis) isomer $\sigma$: 7.52 (s, 1H, olefin), 7.3–7.6 (m, 5H, aromatic), 5.25 (d, 1H, J=1.97 Hz, H-7), 4.76 (d, 1H, J=1.97 Hz, H-6), 4.75 and 5.47 (AB$_q$, 2H, J=13.3 Hz), 3.49 (s, 3H, OCH$_3$), 2.09 (s, 3H, OCOCH$_3$), 1.59 (s, 9H, Bu$^t$).

EXAMPLE-5 t-Butyl-3-acetoxymethyl-3-cephem-7α-methoxy-2-(3-pyridyl)exomethylene-4-carboxylate 1,1-dioxide To a solution of diphenylamine (0.249 g, 0.00147 mol) in dry THF (8 ml) cooled to −15° C. under nitrogen was added n-butyl lithium (0.92 ml, 0.00147 mol, 1.6M in hexane) dropwise. The resulting mixture was stirred at −15° C. for 3 min and then at room temperature for 10 min. The yellowish brown solution was cooled to −78° C. and stirred at this temperature for 10 min at which time the cephalosporanate sulfone (0.592 g, 0.00133 mol) in dry THF (4 ml) was added dropwise and stirred at −78° C. for 5 min. Acetic anhydride (0.38 ml, 0.00399 mol) in THF (2 ml) was added and stirred for 10 min, then pyridine (0.12 ml, 0.00133 mol) was added. The reaction mixture was stirred at −78° C. for 20 min and then allowed to warm to room temperature. Ice water (10 ml) was added to the mixture and extracted with ethyl acetate. The aqueous layer was reextracted with ethyl acetate. The combined ethyl acetate layers were washed with brine, dried (Na$_2$SO$_4$) and concentrated in vacuo to give an oily residue (1.4 g) which was purified over a silica gel column using hexane-ethyl acetate mixture as eluant. Early fractions were the unreacted diphenylamine, aldehydes. Later fractions (270 mg) were a mixture of cis- and trans-isomers which were separated by repeated preparative tlc.

$^1$H NMR (200 MHz, CDCl$_3$) of the major isomer (trans): $\sigma$8.60–8.70 (m, 2H, pyridine), 7.83 (s, 1H, olefin), 7.68 (d, 1H, J=7.83 Hz, pyridine), 7.33–7.48 (m, 1H, pyridine), 5.20 (d, 1H, J=2 Hz), 4.95 (d, 1H, J=2 Hz), 4.93 (d, 1H, J=13.3 Hz, CH$_2$OCOCH$_3$), 4.35 (d, 1H, J=13.3 Hz, CH$_2$OCOCH$_3$), 3.61 (s, 3H, OCH$_3$), 1.93 (s, 3H, OCOCH$_3$), 1.56 (s, 9H, Bu$^t$).

$^1$H NMR (200 MHz, CDCl$_3$) of the minor isomer (cis): $\sigma$8.65–8.70 (m, 2H, pyridine), 8.12 (d, 1H, J=7.79 Hz, pyridine), 7.45 (s, 1H, olefin), 7.45–7.55 (m, 1H, pyridine), 5.52 (d, 1H, J=13.1 Hz, CH$_2$OCOCH$_3$), 5.26 (d, 1H, J=1.52 Hz), 4.82 (d, 1H, J=1.45 Hz), 4.73 (d, 1H, J=13.2 Hz, CH$_2$OCOCH$_3$), 3.53 (s, 3H, OCH$_3$), 2.12 (s, 3H, OCOCH$_3$, 1.60 (s, 9H, Bu$^t$).

EXAMPLE-6 t-Butyl-3-methyl-3-cephem-2-(1-methyl-1,2,3-triazol-4-yl)exomethylene-7α-methoxy4-carboxylate 1,1-dioxide To a solution of diphenylamine (0.533 g, 0.0031193 mol) in dry THF (15 ml) cooled to −10° C. under nitrogen was added n-BuLi (1.949 ml, 0.0031193 mol, 1.6M in hexane). The resulting mixture was stirred at −10° C. for 3 min and then at room temperature for 10 min. The light yellowish brown solution was further cooled to −78° C. and stirred for 10 min during which time t-butyl-3-methyl-3-cephem-7-methoxy-4-carboxylate 1,1-dioxide (0.90 g, 0.002836 mol) in dry THF (10 ml) was added dropwise. The reaction mixture was stirred at −78° C. for 12 min during which time a solution of 1-methyl-1,2,3-triazol-4-yl carboxaldehyde (0.315 g, 0.002836 mol) in dry THF (10 ml) was added dropwise. The mixture was stirred at −78° C. for 5 min; acetic anhydride (1 ml) in THF (5 ml) was added. The yellowish brown solution was stirred at −78° C. for 40 min, dry ice-acetone bath was removed, pyridine (0.8 ml) dissolved in THF (12 ml) was added. After stirring at room temperature for 20 min ethyl acetate (150 ml) was added followed by brine (30 ml). The organic layer was separated, dried (Na$_2$SO$_4$) and the solvent was removed to give an oily mass (1.05 g) which was purified over a silica gel column using a mixture of hexane-ethyl acetate (3:2) as eluant. The minor isomer (cis) was eluted first (180 mg) followed by the major (trans) isomer (440 mg).

$^1$H NMR (200 MHz, CDCl$_3$) of the minor (cis) isomer: $\sigma$8.57 (s, 1H, triazole), 7.46 (s, 1H, olefin), 5.30 (br, s, 1H), 4.77 (br, s, 1H), 4.16 (s, 3H, N—CH$_3$), 3.59 (s, 3H, OCH$_3$), 2.23 (s, 3H, CH$_3$), 1.57 (s, 9H, Bu$^t$).

$^1$H NMR (200 MHz, CDCl$_3$) of the major (trans) isomer: $\sigma$7.85 (s, 1H, triazole), 7.64 (s, 1H, olefin), 5.03 (d, 1H, J=1.5 Hz), 4.81 (d, 1H, J=1.5 Hz), 4.18 (s, 3H, N—CH$_3$), 3.57 (s, 3H, OCH$_3$), 2.30 (s, 3H, CH$_3$), 1.57 (s, 9H, Bu$^t$).

EXAMPLE-7 t-Butyl-3-methyl-3-cephem-2-(methyl)exomethylene-7α-methoxy-4-carboxylate 1,1-dioxide To a stirred solution of diphenylamine (471 mg, 0.0028 mol) in dry THF (15 ml) cooled to −10° C. under nitrogen was added n-BuLi (1.75 ml, 0.0028 mol, 1.6 (M) in hexane). The resulting mixture was stirred at −10° C. for 5 min and then at room temperature for 10 min. The light green solution was cooled to −78° C. and stirred at this temperature for 10 min; t-butyl-3-methyl-3-cephem-7α-methoxy-4-carboxylate, 1,1-dioxide (0.80 g, 0.0025 mol) in dry THF (10 ml) was added dropwise. The mixture was stirred at −78° C. for 10 min, acetaldehyde (0.111 g, 0.0025 mol) in dry THF (3 ml) was added dropwise. The resulting reaction mixture was stirred at −78° C. for 10 min and then acetic anhydride (0.8 ml) in THF (3 ml) was added dropwise. The light yellow colored solution was stirred at −78° C. for 40 min, dry ice-acetone bath was removed, pyridine (0.6 ml) was added. After stirring at room temperature for 20 min, ethyl acetate (150 ml) was added followed by brine (50 ml). The organic layer was separated, dried (Na$_2$SO$_4$) and concentrated to give a crude product (1.2 g) which was purified over a silica gel column using hexane-ethyl acetate (3:2) as eluant. The desired exomethylene product (223 mg) was obtained as a mixture of trans (major) and cis (minor) isomers.

$^1$H NMR (200 MHz, CDCl$_3$) spectrum of cis (minor) isomer: $\sigma$6.62 (q, 1H, J=7.9 Hz, olefin), 5.05 (d, 1H, J=1.5 Hz), 4.7 (d, 1H, J=1.5 Hz), 3.55 (s, 3H, OCH$_3$), 2.41 (d, 3H, J=7.9 Hz, C=CHCH$_3$), 2.06 (s, 3H, CH$_3$), 1.56 (s, 9H, Bu$^t$).

$^1$H NMR (200 MHz, CDCl$_3$) spectrum of trans (major) isomer: $\sigma$7.05 (q, 1H, J=7.0 Hz, olefin), 5.24 (d, 1H, J=1.5 Hz), 4.7 (d, 1H, J=1.5 Hz), 3.57 (s, 3H, OCH$_3$), 2.29 (s, 3H, CH$_3$), 2.1 (d, 3H, J=7.0 Hz, C=CHCH$_3$), 1.56 (s, 9H, Bu$^t$).

EXAMPLE-8 t-Butyl-3-acetoxymethyl-3-cephem-7α-methoxy-2-(2-furyl)exomethylene-4-carboxylate 1,1-dioxide To a solution of diphenylamine (0.498 g, 0.00294 mol) in dry THF (16 ml) cooled to −10° C. was added dropwise n-butyl lithium (1.84 ml, 0.00294 mol, 1.6M in hexane under nitrogen). After the addition was over, the mixture was stirred at room temperature for 15 min, cooled to −78° C.; a solution of cephem sulfone (1.0 g, 0. 00267 mol) in dry THF (8 ml) was added dropwise and the resulting solution was stirred for 15 min. To this mixture was added a solution of 2-furaldehyde (0.334 g, 0.00347 mol) in dry THF (12 ml). The reaction mixture was stirred at −78° C. for 20 min, the cooling bath was removed and stirred for 10 min. The resulting brown solution was cooled to −78° C., acetic anhydride (0.76 ml, 0.008 mol) in dry THF (4 ml) was added. After stirring for 10 min, pyridine (0.24 ml, 0.00297 mol) was added, stirred for 15 min and then at room temperature for 1 h; ice water (25 ml) was added and the mixture was extracted with ethyl acetate (150 ml). The aqueous layer was reextracted with ethyl acetate. The combined ethyl acetate extracts were washed with brine, dried (Na$_2$SO$_4$) and concentrated to give a crude mass (2.2 g) which was purified over a silica gel column using hexane-ethyl acetate (2:1) mixture as eluant.

Early fractions were diphenylamine and 2-furaldehyde. The minor isomer (85 mg) was eluted next followed by major isomer (350 mg). Latter fractions gave unreacted cephem sulfone (440 mg).

$^1$H NMR (200 MHz, CDCl$_3$) of the major (trans) isomer: $\sigma$7.64 (d, 1H, J=1.5 Hz, furan), 7.46 (s, 1H, olefin), 6.90 (d, 1H, J=3.5 Hz, furan), 6.59 (dd, 1H, J=1.5 and 3.5 Hz), 5.08 and 5.43 (AB$_q$, 2H, J=13.0 Hz), 5.04 (d, 1H, J=2 Hz), 4.79 (d, 1H, J=2 Hz), 3.57 (s, 3H, OCH$_3$), 1.93 (s, 3H, OCOCH$_3$), 1.58 (s, 9H, Bu$^t$).

$^1$H NMR (200 MHz, CDCl$_3$) of the minor (cis) isomer: $\sigma$7.65 (d, 1H, J=1.5 Hz, furan), 7.51 (d, 1H, J=3.5 Hz, furan), 7.12 (s, 1H, olefin), 6.6 (dd, 1H, J=1.5 and 3.5 Hz), 5.32 (d, 1H, J=2 Hz), 4.77 and 5.42 (AB$_q$, 2H, J=13.0 Hz), 4.76 (d, 1H, J=2 Hz), 3.58 (s, 3H, OCH$_3$, 2.09 (s, 3H, OCOCH$_3$), 1.58 (s, 9H, Bu$^t$).

What is claimed:

1. A compound of the structural formula I:

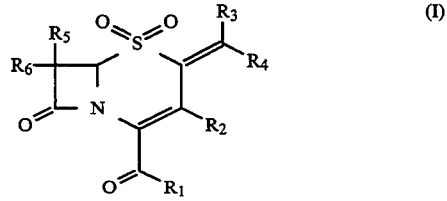

wherein R$_1$ is OR$_a$
  wherein R$_a$ is selected from the group consisting of an unsubstituted or substituted C$_{1-6}$ alkyl group, an unsubstituted or substituted C$_{2-6}$ alkenyl group, an unsubstituted or substituted C$_{2-6}$ alkynyl, an unsubstituted or substituted C$_{3-6}$ cycloalkyl, a C$_{1-6}$ alkoxy C$_{1-6}$ alkyl group, a C$_{1-6}$ alkanoyl C$_{1-6}$ alkyl group, a C$_{1-6}$ alkanoyloxy C$_{1-6}$ alkyl group, C$_{6-10}$ aryl group, a C$_{6-10}$ aryl C$_{1-6}$ alkyl group, a saturated or unsaturated monocyclic or fused polycyclic 3–8 membered heterocyclic group or heterocyclic C$_{1-6}$ alkyl group containing at least one hetero atom selected from O, S or N; said substituted groups being substituted with chloro, bromo, fluoro, hydroxy, C$_{1-6}$ alkoxy, amino, mercapto, nitro, cyano, carboxy, carboxamide, N-substituted carboxamide, sulfinyl, sulfonyl or C$_{1-6}$ alkoxycarbonyl;

wherein R$_2$ is:
  (1) hydrogen;
  (2) chloro, bromo or fluoro; or
  (3) a member selected from the group consisting of a C$_{1-6}$ alkyl group, an unsubstituted or substituted C$_{2-6}$ alkenyl group, an unsubstituted or substituted C$_{2-6}$ alkynyl group and a C$_{3-8}$ cycloalkyl group said substituted groups being substituted with chloro, bromo, fluoro, hydroxy, C$_{1-6}$ alkoxy, amino, mercapto, nitro, cyano, carboxy, carboxamide, N-substituted carboxamide, sulfinyl, sulfonyl or $C_{1-6}$ alkoxycarbonyl;

(4) —$OR_d$ wherein $R_d$ is:
(a) hydrogen; or
(b) a member selected from the group consisting of
a $C_{1-6}$ alkyl group, a $C_{3-8}$ cycloalkyl group, a $C_{6-10}$ aryl group;
a $C_{6-10}$ aryl $C_{1-6}$ alkyl group and an aromatic heterocyclic or heterocyclic $C_{1-6}$ alkyl group having
a saturated or unsaturated monocyclic or fused polycyclic 3-8 membered heterocyclic group containing at least one hetero atom selected from O, S or N (5) —$S(O)_nR_d$
wherein n is 0, 1 or 2 and $R_d$ is as previously defined;
(6) —CHO;
(7) —COOH;
(8) —$C(O)R_d$, wherein $R_d$ is as previously defined;
(9) —$CH_2$—O—$R_d$, wherein $R_d$ is as previously defined;
(10) —$CH_2$—$S(O)_n$—Rd, wherein n is 0, 1 or 2 and $R_d$ is as previously defined;
(11) —$CH_2$—$OC(O)R_d$, wherein $R_d$ is as previously defined;
(12) —$CH_2$—$SC(O)R_d$, wherein $R_d$ is as previously defined;
(13) —$CH_2OC(O)NH_2$;
(14) —$CH_2NR_dR_e$
wherein $R_d$ is as previously defined and $R_e$ is defined the same as $R_d$;
(15) —$CH_2NR_dR_eR_f$
wherein $R_d$ and $R_e$ are as previously defined and $R_f$ is defined the same as $R_d$;
(16) —$CH_2$—NH—$C(O)R_d$, wherein $R_d$ is as previously defined;
or
(17) —$CH_2$—$S(O)_n$—Het, wherein n is 0, 1 or 2 and Het is selected from the group consisting of:

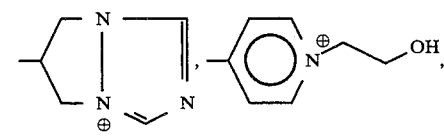

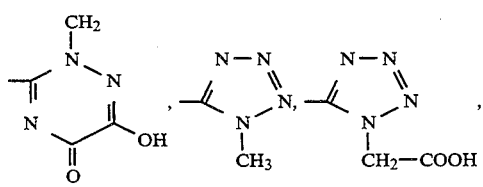

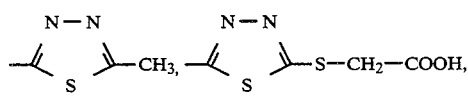

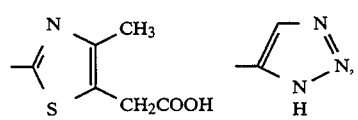

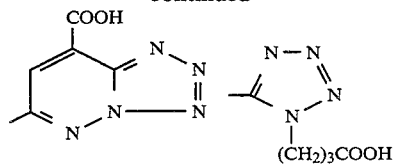

(18) $CH_2NR_dR_eR_f$ wherein $R_d$, $R_e$ and $R_f$ are defined above and are the same or different, or $R_e$ and $R_f$ together with the nitrogen atom form a heterocyclic ring selected from the group consisting of

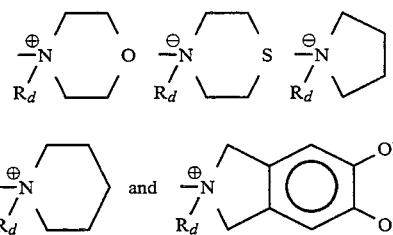

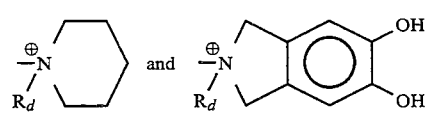

and $R_d$ is as defined above or wherein $R_d$, $R_e$ and $R_f$ together with the nitrogen atom form a heterocyclic or heteroaromatic ring selected from the group consisting of

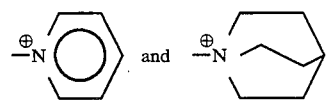

(19) a member selected from the group consisting of

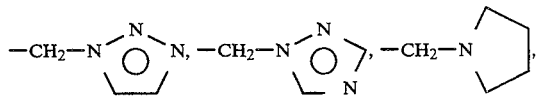

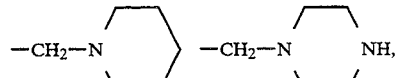

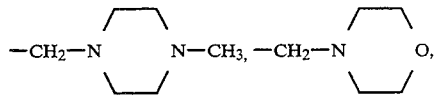

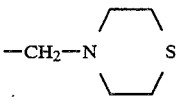

wherein $R_3$ and $R_4$, which are the same or different, are:
(1) hydrogen, provided that $R_3$ and $R_4$ are not both hydrogen;
(3) a $C_{6-10}$ aryl;
(4) a $C_{3-8}$ cycloalkyl;
(5) a saturated or unsaturated monocyclic or fused polycyclic heterocyclic group with 3 to 8 carbon atoms and containing at least one hetero atom selected from the group consisting of O, S and N;
(6) a halogenated $C_{1-6}$ alkyl;

(7) a hydroxy $C_{1-6}$ alkyl;
(8) —$CH_2COOC_{1-6}$ alkyl; or
(9) —$CH_2COOH$;
wherein $R_5$ is:
(1) hydrogen;
(2) chloro, fluoro, bromo or iodo;
(3) a $C_{1-6}$ alkyl group;
(4) a $C_{2-6}$ alkenyl group;
(5) —OH
(6) —$OR_g$, wherein $R_g$ is the same as $R_d$;
(7) —$OC(O)R_g$, wherein $R_g$ is as previously defined;
(8) —$OSO_2R_g$, wherein $R_g$ is as previously defined;
(9) —$NHC(O)R_g$, wherein $R_g$ is as previously defined;
(10) NH—Z, wherein Z is hydrogen or a mono, di- or tri-peptide composed of D or L amino acids with a terminal amino group either free or acylated by —$C(O)R_g$ or —$C(O)OR_g$, wherein $R_g$ is as previously defined; or
(11) —$S(O)_nR_g$, wherein n is 0, 1 or 2 and $R_g$ is as previously defined; and
wherein $R_6$ is:
(1) hydrogen;
(2) chloro or bromo; or
(3) methoxy or methylthio, and pharmaceutically acceptable salts thereof.

2. The compound according to claim 1, wherein $R_1$ is selected from the group consisting of methoxy, ethoxy, isopropoxy, t-butoxy, allyloxy, methoxyethyloxy, benzyloxy, p-nitrobenzyloxy, p-methoxybenzyloxy, diphenylmethyloxy, and 2,2,2 trichloroethyloxy.

3. The compound according to claim 1, wherein $R_2$ is selected from the group consisting of:

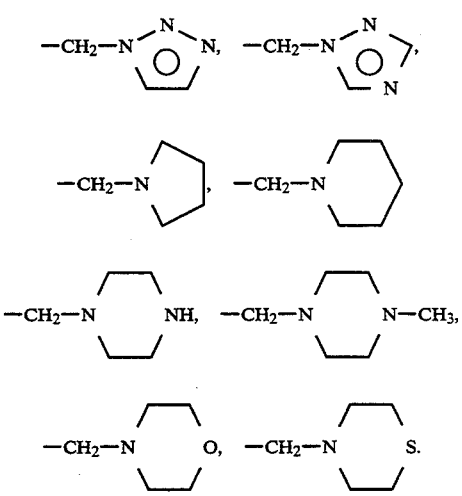

4. The compounds according to claim 1, wherein in said formula —$CH_2NR_dR_eR_f$, $R_e$ and $R_f$ together with the nitrogen atom form a heterocyclic ring selected from the group consisting of

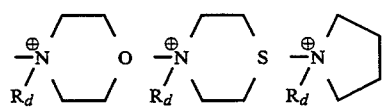

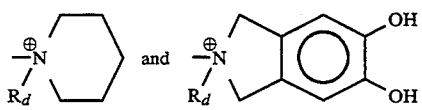

and $R_d$ is as defined above.

5. The compound according to claim 1, wherein in said formula —$CH_2NR_dR_eR_f$, $R_d$, $R_e$ and $R_f$ together with the nitrogen atom form a heteroaromatic ring or a heterocyclic ring selected from the group consisting of

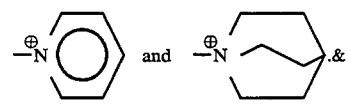

6. The compound according to claim 5, wherein said heteroaromatic ring is:

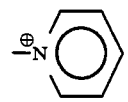

7. The compound according to claim 5, wherein said heterocyclic ring is:

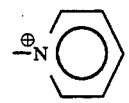

8. The compound according to claim 1, wherein $R_2$ is selected from the group consisting of chloromethyl, bromomethyl and trifluoromethyl.

9. The compound according to claim 1, wherein $R_2$ is selected from the group consisting of hydrogen, methyl, hydroxy, methoxy, vinyl, cyclopropyl, methylthio, acetoxymethyl, hydroxymethyl, chloromethyl, bromomethyl, carbamoyloxymethyl, methoxymethyl, phenoxymethyl, 3-pyridyloxymethyl, methylsulfonylmethyl, phenylsulfonylmethyl, (1,2,3-triazol-1-yl)methyl, (1,2,4-triazol-1-yl)methyl, and aminomethyl.

10. The compound according to claim 1, wherein $R_2$ is a quaternaryammonium methyl selected from the group consisting of:

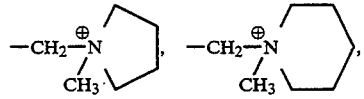

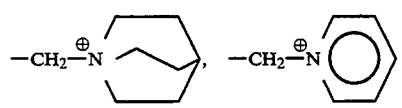

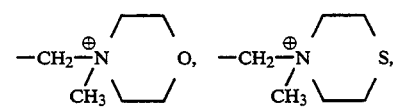

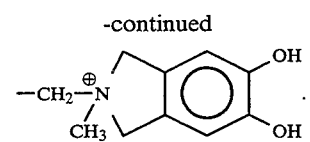

11. The compound according to claim 1, wherein $R_3$ is a saturated or unsaturated monocyclic or fused polycyclic 2 to 8 membered heterocyclic group containing at least one hetero atom selected from the group consisting of O, S and N and $R_4$ is
(1) hydrogen;
(2) a $C_{1-6}$ alkyl group;
(3) a $C_{6-10}$ aryl group;
(4) a $C_{3-8}$ cycloalkyl group;
(5) a $C_{6-10}$ aryl $C_{1-6}$ alkyl group;
(6) a halogenated $C_{1-6}$ alkyl group;
(7) a hydroxy $C_{1-6}$ alkyl group;
(8) —$CH_2COOC_{1-6}$ alkyl; or
(9) —$CH_2COOH$.

12. The compound according to claim 1, wherein $R_4$ is a saturated or unsaturated monocyclic or fused polycyclic 3 to 8 membered heterocyclic group containing at least one hetero atom selected from the group consisting of O, S and N and $R_3$ is
(1) hydrogen;
(2) a $C_{1-6}$ alkyl group;
(3) a $C_{6-10}$ aryl group;
(4) a $C_{3-8}$ cycloalkyl group;
(5) a $C_{6-10}$ aryl $C_{1-6}$ alkyl group;
(6) a halogenated $C_{1-6}$ alkyl group;
(7) a hydroxy $C_{1-6}$ alkyl group;
(8) —$CH_2COOC_{1-6}$ alkyl; or
(9) —$CH_2COOH$.

13. The compound according to claim 1, wherein $R_3$ is selected from the group consisting of methyl, isopropyl, t-butyl, cyclopropyl, phenyl, pyridyl, thienyl, furyl, N-methyl pyrrolyl, pyrazinyl, pyrimidinyl, quinolyl, isoquinolyl, oxazolyl, isoxazolyl, thiazolyl, isothiazolyl, 1-methyl-1,2,3-triazol-4-yl, 1-(2-hydroxyethyl)-1,2,3-traizol-4-yl, 1-(2-pyridinoethyl)-1,2,3-triazol-4-yl, 1-(2-morpholinoethyl)-1,2,3-triazol-4-yl, 1-(2-piperidinoethyl)-1,2,3-triazol-4-yl, and 1-(2-piperazinyl ethyl)-1,2,3-triazol-4-yl.

14. The compound according to claim 1, wherein $R_4$ is selected from the group consisting of methyl, isopropyl, t-butyl, cyclopropyl, phenyl, pyridyl, thienyl, furyl, N-methyl pyrrolyl, pyrazinyl, pyrimidinyl, quinolyl, isoquinolyl, oxazolyl, isoxazolyl, thiazolyl, isothiazolyl, 1-methyl-1,2,3-triazol-4-yl, 1-(2-hydroxyethyl)-1,2,3-triazol-4-yl, 1-(2-pyridinoethyl)-1,2,3-triazol-4-yl, 1-(2-morpholinoethyl)-1,2,3-triazol-4-yl, 1-(2-piperidinoethyl)-1,2,3-triazol-4-yl, and 1-(2-piperazinyl ethyl)-1,2,3-triazol-4-yl.

15. The compound according to claim 1, wherein $R_5$ is selected from the group consisting of methoxy, ethoxy, methyl, ethyl, vinyl, formamido, acetamido, trifluoroacetamido, acetyloxy, chloroacetyloxy, bromoacetyloxy, methylsulfonyloxy, phenylsulfonyloxy and tolylsulfonyloxy.

16. The compound according to claim 1 which is t-butyl-3-acetoxymethyl-3-cephem-2-(1-methyl-1,2,3-triazol-4-yl)exomethylene-7α-methoxy-4-carboxylate-1,1-dioxide.

17. The compound according to claim 1 which is t-butyl-3-acetoxymethyl-3-cephem-2-(2-fluorophenyl-)exomethylene-7α-methoxy-4-carboxylate-1,1-dioxide.

18. The compound according to claim 1 which is t-butyl-3-acetoxymethyl-3-cephem-2-(3-thienyl)exomethylene-7α-methoxy-4-carboxylate-1,1-dioxide.

19. The compound according to claim 1 which is t-butyl-3-acetoxymethyl-3-cephem-2-(phenyl)exomethylene-7α-methoxy-4-carboxylate-1,1-dioxide.

20. The compound according to claim 1 which is t-butyl-3-acetoxymethyl-3-cephem-2-(3-pyridyl)exomethylene-7α-methoxy-4-carboxylate-1,1-dioxide.

21. The compound according to claim 1 which is t-butyl-3-methyl-3-cephem-2-(1-methyl-1,2,3-triazol-4-yl)exomethylene-7α-methoxy-4-carboxylate-1,1-dioxide.

22. The compound according to claim 1 which is t-butyl-3-methyl-3-cephem-2-(methyl)exomethylene-7α-methoxy-4-carboxylate-1,1-dioxide.

23. The compound according to claim 1 which is t-butyl-3-acetoxymethyl-3-cephem-2-(2-furyl)exomethylene-7α-methoxy-4-carboxylate-1,1-dioxide.

24. A pharmaceutical composition suitable for the treatment of thrombosis, inflammatory or degenerative diseases comprising an effective amount of the compound of claim 1 and a pharmaceutically acceptable carrier.

25. A method for treating thrombosis in a mammal, comprising:
administering to said mammal an effective anticoagulating amount of the compound according to claim 1.

26. A method for treating inflammatory or degenerative diseases caused by proteolytic enzymes in a mammal, comprising:
administering to said mammal an effective anti-inflammatory or anti-degenerative amount of the compound according to claim 1.

27. A pharmaceutically acceptable ester which hydrolyzes in the human body to produce the compound of claim 1.

28. The pharmaceutical composition according to claim 24, wherein said compound is selected from the group consisting of t-butyl-3-acetoxymethyl-3-cephem-2-(1-methyl-1,2,3-triazol-4-yl)exomethylene-7α-methoxy-4-carboxylate-1,1-dioxide, t-butyl-3-acetoxymethyl-3-cephem-2-(3-pyridyl)exomethylene-7α-methoxy-4-carboxylate-1,1-dioxide, t-butyl-3-acetoxymethyl-3-cephem-2-(3-thienyl)exomethylene-7α-methoxy-4-carboxylate-1,1-dioxide, t-butyl-3-methyl-3-cephem-2-(1-methyl-1,2,3-triazol-4-yl)exomethylene-7α-methoxy-4-carboxylate-1,1-dioxide, and t-butyl-3-acetoxymethyl-3-cephem-2-(2-furyl)exomethylene-7α-methoxy-4-carboxylate-1,1-dioxide.

29. A compound of the structural formula I and pharmaceutically acceptable salts thereof:

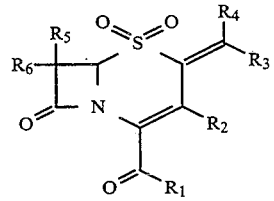

wherein $R_1$ is selected from the group consisting of methoxy, ethoxy, isopropoxy, t-butoxy, allyloxy, methoxyethyloxy, benzyloxy, p-nitrobenzyloxy, p-methoxybenzyloxy, diphenylmethyloxy, and 2,2,2-trichloroethyloxy, R$_2$ is selected from the group consisting of hydrogen, methyl, hydroxy, methoxy, vinyl, cyclopropyl, methylthio, acetoxymethyl, hydroxymethyl, chloromethyl, bromomethyl, trifluoromethyl, carbamoyloxymethyl, methoxymethyl, phenoxymethyl, 3-pyridyloxymethyl, methylsulfonylmethyl, phenylsulfonylmethyl, (1,2,3-triazol-1-yl)methyl, (1,2,4-triazol-1-yl)methyl, aminomethyl, wherein one of R$_3$ or R$_4$ is a saturated or unsaturated monocyclic or fused polycyclic 3 to 8 membered heterocyclic group containing at least one hetero atom selected from the group consisting of O, S and N, and the other is hydrogen;

wherein R$_5$ is selected from the group consisting of methoxy, ethoxy, methyl, ethyl, vinyl, formamido, acetamido, trifluoroacetamido, acetyloxy, chloroacetyloxy, bromoacetyloxy, methylsulfonyloxy, phenylsulfonyloxy and tolylsulfonyloxy, and wherein R$_6$ is:

(1) hydrogen;

(2) chloro or bromo; or (3) methoxy or methylthio.

30. A compound of the structural formula I:

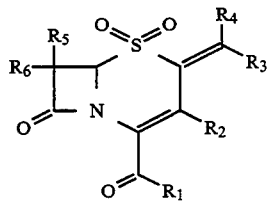

(I)

wherein R$_1$ is OR$_a$ wherein R$_a$ is selected from the group consisting of an unsubstituted or substituted C$_{1-6}$ alkyl group, an unsubstituted or substituted C$_{2-6}$ alkenyl group, an unsubstituted or substituted C$_{2-6}$ alkynyl, an unsubstituted or substituted C$_{3-6}$ cycloalkyl, a C$_{1-6}$ alkoxy C$_{1-6}$ alkyl group, a C$_{1-6}$ alkanoyl C$_{1-6}$ alkyl group, a C$_{1-6}$ alkanoyloxy C$_{1-6}$ alkyl group, C$_{6-10}$ aryl group, a C$_{6-10}$ aryl C$_{1-6}$ alkyl group, a saturated or unsaturated monocyclic or fused polycyclic 3-8 membered heterocyclic group or heterocyclic C$_{1-6}$ alkyl group containing at least one hetero atom selected from O, S or N; said substituted groups being substituted with chloro, bromo, fluoro, hydroxy, C$_{1-6}$ alkoxy, amino, mercapto, nitro, cyano, carboxy, carboxamide, N-substituted carboxamide, sulfinyl, sulfonyl or C$_{1-6}$ alkoxycarbonyl;

wherein R$_2$ is:

(1) hydrogen;

(2) chloro, bromo or fluoro; or (3) a member selected from the group consisting of a C$_{1-6}$ alkyl group, an unsubstituted or substituted C$_{2-6}$ alkenyl group, an unsubstituted or substituted C$_{2-6}$ alkynyl group and a C$_{3-8}$ cycloalkyl group said substituted groups being substituted with chloro, bromo, fluoro, hydroxy, C$_{1-6}$ alkoxy, amino, mercapto, nitro, cyano, carboxy, carboxamide, N-substituted carboxamide, sulfinyl, sulfonyl or C$_{1-6}$ alkoxycarbonyl;

(4) —OR$_d$ wherein R$_d$ is:

(a) hydrogen; or (b) a member selected from the group consisting of a C$_{1-6}$ alkyl group, a C$_{3-8}$ cycloalkyl group, a C$_{6-10}$ aryl group;

a C$_{6-10}$ aryl C$_{1-6}$ alkyl group and an aromatic heterocyclic or heterocyclic C$_{1-6}$ alkyl group having a saturated or unsaturated monocyclic or fused polycyclic 3-8 membered heterocyclic group containing at least one hetero atom selected from O, S or N (5) —S(O)$_n$R$_d$ wherein n is 0, 1 or 2 and R$_d$ is as previously defined;

(6) —CHO;

(7) —COOH;

(8) —C(O)R$_d$, wherein R$_d$ is as previously defined;

(9) —CH$_2$—O—R$_d$, wherein R$_d$ is as previously defined;

(10) —CH$_2$—S(O)$_n$—R$_d$, wherein n is 0, 1 or 2 and R$_d$ is as previously defined;

(11) —CH$_2$—OC(O)R$_d$, wherein R$_d$ is as previously defined;

(12) —CH$_2$—SC(O)R$_d$, wherein R$_d$ is as previously defined;

(13) —CH$_2$OC(O)NH$_2$;

(14) —CH$_2$NR$_d$R$_e$ wherein R$_d$ is as previously defined and R$_e$ is defined the same as R$_d$;

(15) —CH$_2$NR$_d$R$_e$R$_f$ wherein R$_d$ and R$_e$ are as previously defined and R$_f$ is defined the same as R$_d$;

(16) —CH$_2$—NH—C(O)R$_d$, wherein R$_d$ is as previously defined;

or

(17) —CH$_2$—S(O)$_n$—Het, wherein n is 0, 1 or 2 and Het is selected from the group consisting of:

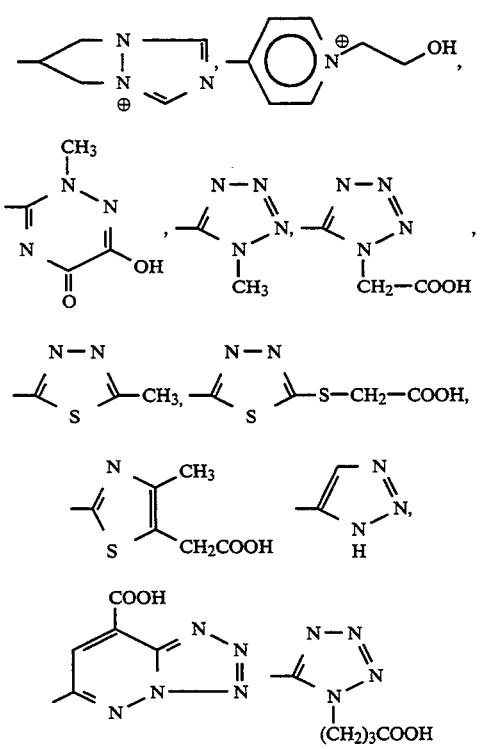

(18) CH$_2$NR$_d$R$_e$R$_f$ wherein R$_d$, R$_e$ and R$_f$ are defined above and are the same or different, or R$_e$ and R$_f$ together with the nitrogen atom form a heterocyclic ring selected from the group consisting of

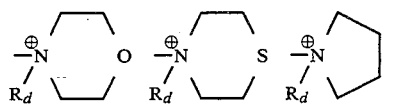

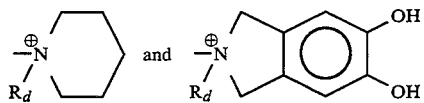

and R<sub>d</sub> is as defined above or wherein $R_d$, $R_e$ and $R_f$ together with the nitrogen atom form a heterocyclic or heteroaromatic ring selected from the group consisting of

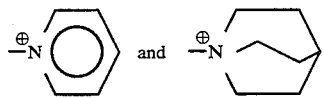

(19) a member selected from the group consisting of

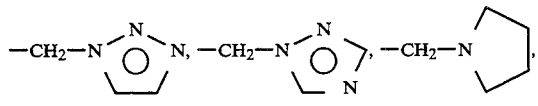

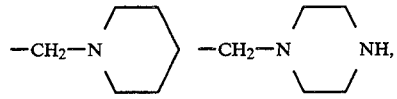

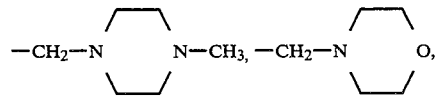

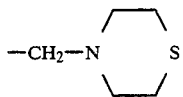

wherein $R_3$ and $R_4$, which are the same or different, and wherein one of $R_3$ and $R_4$ is a saturated or unsaturated monocyclic or fused polycyclic heterocyclic group with 3 to 8 carbon atoms and containing at least one hetero atom selected from the group consisting of O, S and N; and the other may be a second heterocyclic group as defined above, or the other may be selected from the group consisting of:
- (1) hydrogen,
- (2) a $C_{1-6}$ alkyl;
- (3) a $C_{6-10}$ aryl;
- (4) a $C_{3-8}$ cycloalkyl;
- (5) a halogenated $C_{1-6}$ alkyl;
- (6) a hydroxy $C_{1-6}$ alkyl;
- (7) —CH$_2$COOC$_{1-6}$ alkyl; or
- (8) —CH$_2$COOH;

wherein $R_5$ is:
- (1) hydrogen;
- (2) chloro, fluoro, bromo or iodo;
- (3) a $C_{1-6}$ alkyl group;
- (4) a $C_{2-6}$ alkenyl group;
- (5) —OH
- (6) —OR$_g$, wherein $R_g$ is the same as $R_d$;
- (7) —OC(O)R$_g$, wherein $R_g$ is as previously defined;
- (8) —OSO$_2$R$_g$, wherein $R_g$ is as previously defined;
- (9) —NHC(O)R$_g$, wherein $R_g$ is as previously defined;
- (10) NH—Z, wherein Z is hydrogen or a mono, di- or tri-peptide composed of D or L amino acids with a terminal amino group either free or acylated by —C(O)R$_g$ or —C(O)OR$_g$, wherein $R_g$ is as previously defined; or
- (11) —S(O)$_n$R$_g$, wherein n is 0, 1 or 2 and $R_g$ is as previously defined; and wherein $R_6$ is:
- (1) hydrogen;
- (2) chloro or bromo; or
- (3) methoxy or methylthio, and pharmaceutically acceptable salts thereof.

* * * * *

UNITED STATES PATENT AND TRADEMARK OFFICE
CERTIFICATE OF CORRECTION

PATENT NO. : 5,446,037
DATED : August 29, 1995
INVENTOR(S) : Maiti et al.

It is certified that error appears in the above-indentified patent and that said Letters Patent is hereby corrected as shown below:

Column 12, line 42, delete "$Bu^t$" and substitute therefor --$OBu^t$-- and delete "OAc" and substitute therefor --$CH_2OAc$--;

line 48, delete "$Bu^t$" and substitute therefor --$OBu^t$-- and delete "OAc" and substitute therefor --$CH_2OAc$--;

line 54, delete "$Bu^t$" and substitute therefor --$OBu^t$-- and delete "OAc" and substitute therefor --$CH_2OAc$--;

line 60, delete "$Bu^t$" and substitute therefor --$OBu^t$-- and delete "OAc" and substitute therefor --$CH_2OAc$--;

line 66, delete "$Bu^t$" and substitute therefor --$OBu^t$-- and delete "OAc" and substitute therefor --$CH_2OAc$--.

UNITED STATES PATENT AND TRADEMARK OFFICE
CERTIFICATE OF CORRECTION

PATENT NO. : 5,446,037
DATED : August 29, 1995
INVENTOR(S) : Maiti et al.

It is certified that error appears in the above-indentified patent and that said Letters Patent is hereby corrected as shown below:

Column 13, line 15, delete "$Bu^t$" and substitute therefor --$OBu^t$-- and delete "OAc" and substitute therefor --$CH_2OAc$--;

line 20, delete "$Bu^t$" and substitute therefor --$OBu^t$-- and delete "OAc" and substitute therefor --$CH_2OAc$--;

line 24, delete "$Bu^t$" and substitute therefor --$OBu^t$-- and delete "OAc" and substitute therefor --$CH_2OAc$--;

line 27, delete "$Bu^t$" and substitute therefor --$OBu^t$--;

line 33, delete "$Bu^t$" and substitute therefor --$OBu^t$--;

line 38, delete "$Bu^t$" and substitute therefor --$OBu^t$-- and delete "OAc" and substitute therefor --$CH_2OAc$--;

UNITED STATES PATENT AND TRADEMARK OFFICE
CERTIFICATE OF CORRECTION

PATENT NO. : 5,446,037
DATED : August 29, 1995
INVENTOR(S) : Maiti et al.

It is certified that error appears in the above-indentified patent and that said Letters Patent is hereby corrected as shown below:

line 43, delete "Bu$^t$" and substitute therefor --OBu$^t$-- and delete "OAc" and substitute therefor --CH$_2$OAc--;

line 48, delete "Bu$^t$" and substitute therefor --OBu$^t$--;

line 53, delete "Bu$^t$" and substitute therefor --OBu$^t$--.

Signed and Sealed this

Twenty-third Day of January, 1996

Attest:

BRUCE LEHMAN

*Attesting Officer*     *Commissioner of Patents and Trademarks*